United States Patent [19]

Niemers et al.

[11] Patent Number: 4,491,595
[45] Date of Patent: Jan. 1, 1985

[54] COMBATING FUNGI WITH TRISUBSTITUTED CYANOGUANIDINES

[75] Inventors: Ekkehard Niemers; Winfried Lunkenheimer, both of Wuppertal; Wilhelm Brandes, Leichlingen, all of Fed. Rep. of Germany

[73] Assignee: Bayer Aktiengesellschaft, Leverkusen, Fed. Rep. of Germany

[21] Appl. No.: 249,249

[22] Filed: Mar. 30, 1981

[30] Foreign Application Priority Data

Apr. 15, 1980 [DE] Fed. Rep. of Germany ....... 3014353

[51] Int. Cl.³ .................... C07C 129/12; A01N 37/52
[52] U.S. Cl. ................. 424/326; 260/465 E; 260/465.5 R; 260/501.14; 544/105; 544/106; 546/163; 546/230; 546/246; 548/482; 548/369; 564/86; 564/104; 424/248.56; 424/256; 424/258; 424/274; 424/304; 424/320
[58] Field of Search .............. 564/86, 104; 260/465 E, 260/465.5 R, 326.62, 326.15, 501.14; 546/246, 230, 163; 544/105, 106; 424/326, 304, 274, 248.56, 256, 258, 320; 548/309, 482

[56] References Cited

U.S. PATENT DOCUMENTS

| 4,049,672 | 9/1977 | Durant et al. ........................ 548/342 |
| 4,138,561 | 2/1979 | Crenshaw et al. ................... 544/284 |
| 4,158,013 | 6/1979 | Crenshaw et al. ................... 564/104 |
| 4,250,092 | 2/1981 | Kajfez et al. ..................... 260/239 E |
| 4,276,421 | 6/1981 | Baudet ................................ 548/342 |

FOREIGN PATENT DOCUMENTS

| 2318986 | 5/1972 | Fed. Rep. of Germany ...... 424/326 |
| 2855836 | 7/1979 | Fed. Rep. of Germany ...... 424/326 |
| 2425429 | 5/1979 | France ................................. 424/326 |
| 472001 | 7/1979 | Spain .................................. 564/104 |

OTHER PUBLICATIONS

Chemical Abstracts, vol. 67, 1967, p. 9352.
Chemical Abstracts, vol. 94, No. 7, 2/16/81.
J. Chem. Eng. Data 1981, 26 (1), pp. 105-106.
Petersen, J. Med. Chem. 21, 773, (1978).
Schönecker, J. Prukt. Chemie 318, 483, (1976).
Andersen, Can. J. Chem. 49, 2315, (1971).

*Primary Examiner*—Robert Gerstl
*Attorney, Agent, or Firm*—Sprung, Horn, Kramer & Woods

[57] ABSTRACT

Trisubstituted cyanoguanidines of the formula

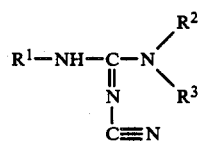

in which
R¹ represents an optionally substituted phenyl or phenylalkyl radical, an alkyl radical with more than 1 carbon atom, a substituted alkyl radical, an alkenyl or alkinyl radical or an optionally substituted cycloalkyl radical,
R² represents an optionally substituted alkyl radical or an alkenyl or alkinyl radical and
R³ represents an optionally substituted alkyl radical, an alkenyl or alkinyl radical, an optionally substituted cycloalkyl radical or an optionally substituted phenyl or phenylalkyl radical, or
R² and R³, together with the nitrogen atom to which they are bonded, represent an optionally substituted heterocyclic radical, which optionally contains an oxygen atom as a further hetero-atom, or a physiologically acceptable acid addition salt thereof, which possess fungicidal properties. Processes for their preparation are also taught.

8 Claims, No Drawings

COMBATING FUNGI WITH TRISUBSTITUTED CYANOGUANIDINES

The present invention relates to certain new trisubstituted cyanoguanidines, to several processes for their production and to their use as fungicides.

It has already been disclosed that N-chloroacetyl-N-(2,6-dialkylphenyl)-alanine esters, such as N-chloroacetyl-N-(2-ethyl-6-methyl-phenyl)-alanine ethyl ester, can be employed with good success for combating fungal diseases of plants (see DE-OS (German Published Specification) No. 2,350,944). However, their action is not always completely satisfactory, especially when low amounts and concentrations are applied and in particular when they are used for combating Phytophthora species.

The present invention now provides, as new compounds, the trisubstituted cyanoguanidines of the general formula

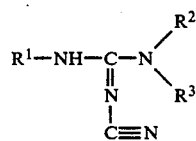
(I)

in which
R$^1$ represents an optionally substituted phenyl or phenylalkyl radical, an alkyl radical with more than one carbon atom, a substituted alkyl radical, an alkenyl or alkinyl radical or an optionally substituted cycloalkyl radical,
R$^2$ represents an optionally substituted alkyl radical or an alkenyl or alkinyl radical and
R$^3$ represents an optionally substituted alkyl radical, an alkenyl or alkinyl radical, an optionally substituted cycloalkyl radical or an optionally substituted phenyl or phenylalkyl radical or
R$^2$ and R$^3$, together with the nitrogen atom to which they are bonded, represent an optionally substituted heterocyclic radical, which optionally contains an oxygen atom as a further hetero-atom, and physiologically acceptable acid addition salts thereof.

The compounds of the formula (I) according to the invention can exist in the following two tautomeric forms:

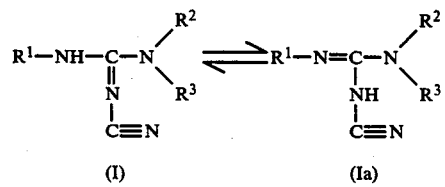

According to the present invention there is further provided a process for the production of a compound of the present invention, characterized in that
(a) a thiourea of the general formula

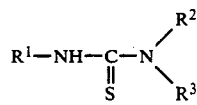
(II)

in which
R$^1$, R$^2$ and R$^3$ have the abovementioned meaning, is reacted with a heavy metal salt of cyanamide in the presence of a diluent and if appropriate in the presence of a phase transfer catalyst, or (b) an amidine of the general formula

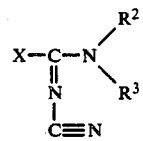
(III)

in which
R$^2$ and R$^3$ have the abovementioned meaning and
X represents a halogen atom or an alkoxy or alkylthio radical,
is reacted with an amine of the general formula $$R^1-NH_2 \quad (IV)$$

in which
R$^1$ has the abovementioned meaning, in the presence of a diluent, or (c) an amidine of the general formula

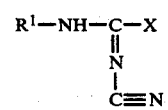
(V)

in which
R$^1$ has the abovementioned meaning and
X represents a halogen atom or an alkoxy or alkylthio radical,
is reacted with an amine of the general formula

(VI)

in which
R$^2$ and R$^3$ have the abovementioned meaning, in the presence of a diluent.

The new trisubstituted cyanoguanidines of the present invention have powerful fungicidal properties. Surprisingly, the compounds according to the invention exhibit a considerably more powerful action than N-chloroacetyl-N-(2-ethyl-6-methyl-phenyl)-alanine ethyl ester, which is known from the state of the art. The substances according to the invention thus represent an enrichment of the art.

Preferred trisubstituted cyanoguanidines according to the present invention are those of formula (I) in which R$^1$ represents a phenyl radical which is optionally monosubstituted or polysubstituted by identical or different substituents, preferred substituents being: halogen, alkyl with 1 or 4 carbon atoms, alkenyl with 2 or 3 carbon atoms, alkoxy and alkylthio with in each case 1 to 4 carbon atoms, halogenoalkyl with 1 or 2 carbon atoms and 1 to 5 identical or different halogen atoms (such as, in particular, fluorine and chlorine atoms), nitro, cyano, amino, alkyl and dialkyl-amino with 1 to 4 carbon atoms in each alkyl part, hydroxyl, alkylcarbonyl and alkylsulphonyl with in each case 1 to 4 carbon atoms in the alkyl part, carbamoyl, aminosulphonyl, and phenyl, phenoxy and benzyloxy which are optionally substituted by halogen or alkyl with 1 or 2 carbon atoms, as well as a group of the general formula —NR$^4$—CO—R$^5$ or —(CH$_2$)$_n$—NR$^6$R$^7$, in which R$^4$, R$^6$ and R$^7$ independently represent hydrogen or alkyl with 1 to 4 carbon atoms, R$^5$ represents alkyl with 1 to 4 carbon atoms and n is 0, 1, 2, 3 or 4, R$^1$ represents a phenylalkyl radical which is optionally substituted in the phenyl part and has 1 or 2 carbon atoms in the alkyl part, preferred substituents being: halogen, alkyl with 1 to 4 carbon atoms, alkoxy and alkylthio with in each case 1 to 4 carbon atoms, halogenoalkyl with 1 or 2 carbon atoms and 1 to 5 identical or different halogen atoms (such as, in particular, fluorine and chlorine atoms), nitro and cyano, R$^1$ represents a straight-chain or branched alkyl radical with 2 to 10 carbon atoms or a substituted straight-chain or branched alkyl radical with 1 to 10 carbon atoms, preferred substituents being: hydroxyl, cyano, alkoxy with 1 to 4 carbon atoms and cyclopropyl, or R$^1$ represents an alkenyl or alkinyl radical with in each case 2 to 10 carbon atoms or a cycloalkyl radical which has 3 to 8 carbon atoms and is optionally substituted by alkyl with 1 or 2 carbon atoms, R$^2$ and R$^3$ independently represent an optionally substituted, straight-chain or branched alkyl radical with 1 to 4 carbon atoms, preferred substituents being: hydroxyl, cyano and alkoxy with 1 to 4 carbon atoms or independently represent alkenyl or alkinyl with in each case 3 to 5 carbon atoms, or R$^3$ additionally represents a cycloalkyl radical which has 5 to 8 carbon atoms and is optionally substituted by alkyl with 1 or 2 carbon atoms, or an optionally substituted phenyl or benzyl radical, preferred substituents being the substituents on phenyl which have already been mentioned as preferred in the case of R$^1$, or R$^2$ and R$^3$ represent, together with the nitrogen atom to which they are bonded, a 5-membered to 7-membered heterocyclic ring which optionally also contains, in addition to the nitrogen atom, an oxygen atom as a further hetero-atom and is optionally substituted by alkyl with 1 or 2 carbon atoms or by a fused-on benzene ring.

Particularly preferred trisubstituted cyanoguanidines of the formula (I) are those in which R$^1$ represents a phenyl radical which is optionally mono-substituted or polysubstituted by identical or different substituents, preferred substituents being: fluorine, chlorine, bromine, iodine, methyl, ethyl, n-propyl, isopropyl, vinyl, methoxy, methylthio, ethoxy, n-propoxy, isopropoxy, trifluoromethyl, nitro, cyano, amino, hydroxy, dimethylamino, acetyl, methylsulphonyl, carbamoyl, aminosulphonyl, phenyl, chlorophenyl, phenoxy, chlorophenoxy, benzyloxy, chlorobenzyloxy, methylaminomethyl, dimethylaminomethyl, methylaminoethyl, dimethylaminoethyl, acetylamino and acetyl-methyl-amino; represents a benzyl or phenethyl radical which is optionally monosubstituted or polysubstituted by identical or different substituents, preferred substituted being: fluorine, chlorine, methyl, ethyl, n-propyl, isopropyl, methoxy, methylthio, trifluoromethyl, nitro and cyano; or represents a cyclopropylmethyl, cyclopropyl, cyclobutyl or cyclopentyl radical, or a cyclohexyl radical which is optionally substituted by methyl or ethyl; R$^2$ represents a methyl, ethyl, n-propyl, isopropyl, hydroxyethyl, cyanoethyl or allyl radical; R$^3$ represents a methyl, ethyl, n-propyl, isopropyl, hydroxyethyl, cyanoethyl, allyl or cyclopentyl radical, a cyclohexyl radical which is optionally substituted by methyl or ethyl, or an optionally substituted phenyl or benzyl radical, preferred substituents being: fluorine, chlorine, bromine, methyl, ethyl, methoxy, nitro and cyano; or R$^2$ and R$^3$, together with the nitrogen atom to which they are bonded, represent pyrrolidine, piperidine or morpholine which is optionally substituted by methyl or a fused-on benzene ring.

The following compounds of the general formula (I) may be mentioned specifically, in addition to the compounds mentioned in the preparative examples hereinbelow:

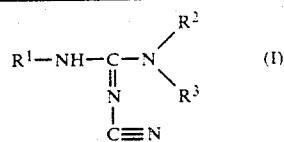
(I)

| R$^1$ | R$^2$ | R$^3$ |
|---|---|---|
| 2,6-Cl$_2$—C$_6$H$_3$ | | —(CH$_2$)$_4$— |
| 2,6-Cl$_2$—C$_6$H$_3$ | CH$_3$ | CH$_3$ |
| 2,6-(CH$_3$)$_2$—C$_6$H$_3$ | C$_3$H$_7$ | C$_3$H$_7$ |
| 2,6-(CH$_3$)$_2$—C$_6$H$_3$ | —CH$_2$—CH=CH$_2$ | —CH$_2$—CH=CH$_2$ |
| 2-CH$_3$—C$_6$H$_4$ | | —(CH$_2$)$_4$— |
| 2-C$_2$H$_5$—C$_6$H$_4$ | | —(CH$_2$)$_4$— |
| 2-i-C$_3$H$_7$—C$_6$H$_4$ | | —(CH$_2$)$_4$— |
| 2,3,6-(CH$_3$)$_3$—C$_6$H$_4$ | | —(CH$_2$)$_4$— |

 —(CH$_2$)$_4$—

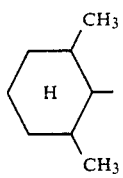 —(CH$_2$)$_4$—

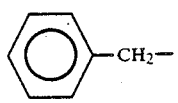 —(CH$_2$)$_4$—

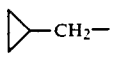 —(CH$_2$)$_4$—

 —(CH$_2$)$_4$—

 —(CH$_2$)$_4$—

 —(CH$_2$)$_4$—

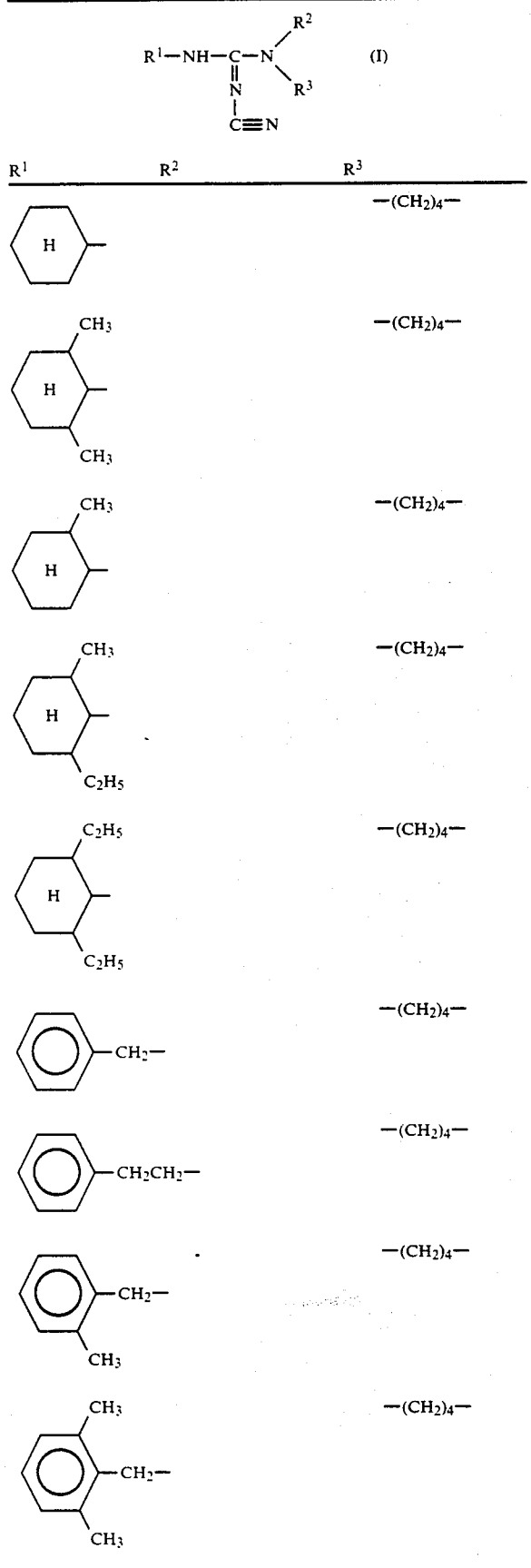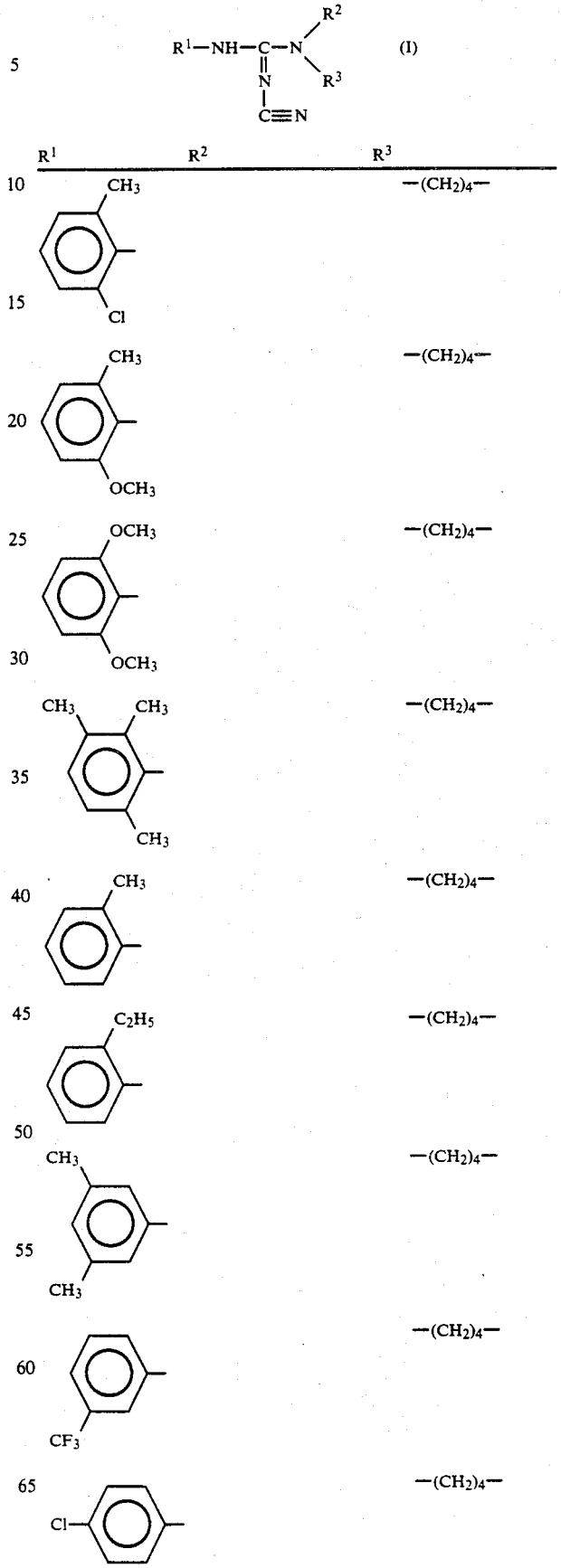

-continued $$R^1-NH-C(=N-C≡N)-N(R^2)(R^3) \quad (I)$$

| $R^1$ | $R^2$ | $R^3$ |
|---|---|---|
| 4-CH₃O-C₆H₄- | | —(CH₂)₄— |
| 4-CH₃-C₆H₄- | | —(CH₂)₄— |
| 3,4-Cl₂-C₆H₃- | | —(CH₂)₄— |
| 3-Cl-C₆H₄- | | —(CH₂)₄— |
| 4-(CH₃)₃C-C₆H₄- | | —(CH₂)₄— |
| 4-(CH₃)₂N-C₆H₄- | | —(CH₂)₄— |
| 4-(CH₃)₂N-3-CH₃-C₆H₃- | | —(CH₂)₄— |
| 4-H₂N-C₆H₄- | | —(CH₂)₄— |
| 4-HO-C₆H₄- | | —(CH₂)₄— |
| 4-CH₃O-3-CH₃-C₆H₃- | | —(CH₂)₄— |
| 4-(CH₃)₂CH-O-C₆H₄- | | —(CH₂)₄— |
| 3-(CH₃)₂N-C₆H₄- | | —(CH₂)₄— |
| 3-NH₂-C₆H₄- | | —(CH₂)₄— |
| 3-Br-C₆H₄- | | —(CH₂)₄— |
| 3-I-C₆H₄- | | —(CH₂)₄— |
| 2-Cl-C₆H₄- | | —(CH₂)₄— |
| 2-OCH₃-C₆H₄- | | —(CH₂)₄— |
| 4-O₂N-C₆H₄- | | —(CH₂)₄— |
| 4-NC-C₆H₄- | | —(CH₂)₄— |
| 4-CH₃CO-C₆H₄- | | —(CH₂)₄— |
| 4-CH₃SO₂-C₆H₄- | | —(CH₂)₄— |

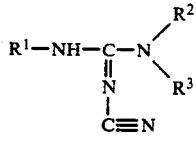

-continued $$R^1-NH-C(=N-C\equiv N)-NR^2R^3 \quad (I)$$

| $R^1$ | $R^2$ | $R^3$ |
|---|---|---|
| 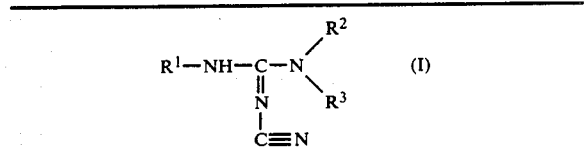 | | $-(CH_2)_4-$ |
| 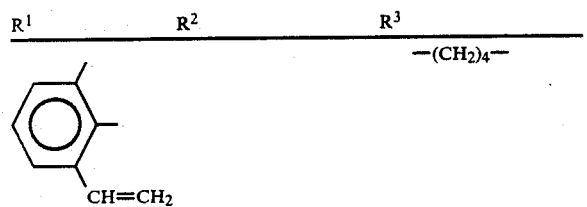 | $-CH(CH_3)_2$ | $-CH(CH_3)_2$ |
| 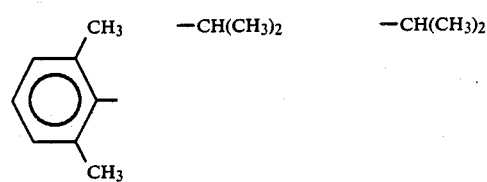 | $-CH_2-CH=CH_2$ | $-CH_2-CH=CH_2$ |
| 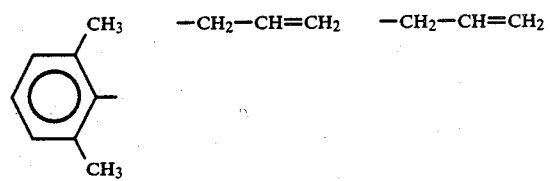 | $-CH_2CH_2OH$ | $CH_3$ |
| 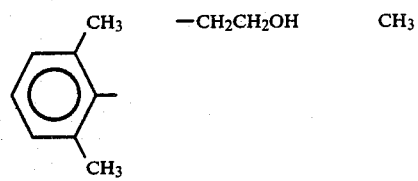 | $-CH_2CH_2OH$ | $-CH_2CH_2OH$ |
| 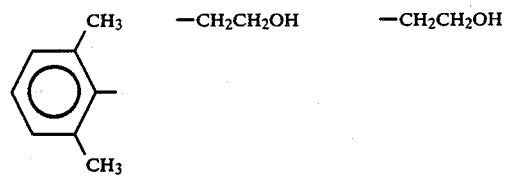 | $-CH_2CH_2OH$ | $CH_3$ |
| 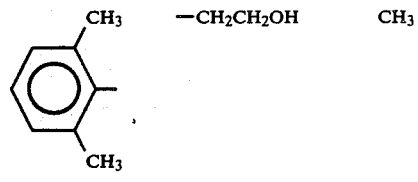 | $CH_3$ | 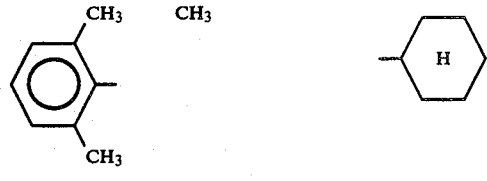 |
| 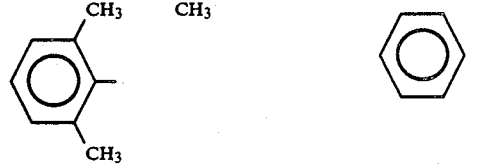 | $CH_3$ | (phenyl) |

-continued $$R^1-NH-C(=N-C\equiv N)-NR^2R^3 \quad (I)$$

| $R^1$ | $R^2$ | $R^3$ |
|---|---|---|
| 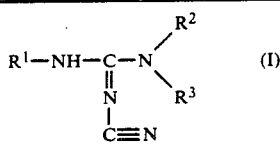 | $CH_3$ | $-CH_2-$(phenyl) |
| 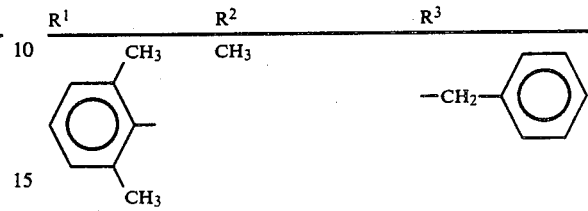 | $CH_3$ | $-CH(CH_3)-(CH_2)_4-$ |
|  | | $-(CH_2)_3-$(o-tolyl) |
|  | | $-CH_2-CH(CH_3)-$(o-tolyl) |
|  | $CH_3$ | $-(CH_2)_6-$ |

If, for example, N'-(2,6-dimethylphenyl)-N,N-tetramethylene-thiourea and lead cyanamide are used as starting substances, the course of the reaction of process variant (a) is illustrated by the following equation:

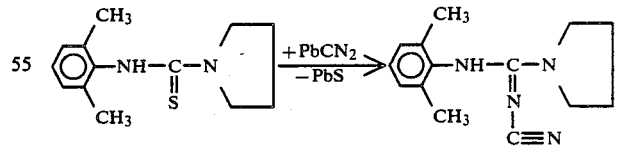

If, for example, N-cyano-N'-dimethyl-S-methyl-isothiourea and benzylamine are used as starting substances, the course of the reaction of process variant (b) is illustrated by the following equation

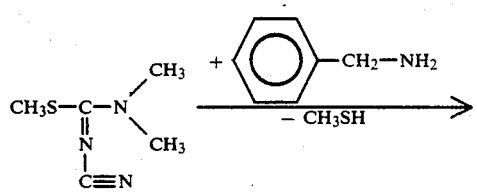

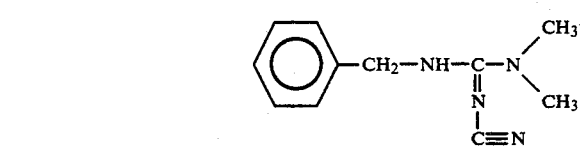

If, for example, N-tert.-butyl-N'-cyano-S-methyl-isothiourea and pyrrolidine are used as starting substances, the course of the reaction of process variant (c) is illustrated by the following equation

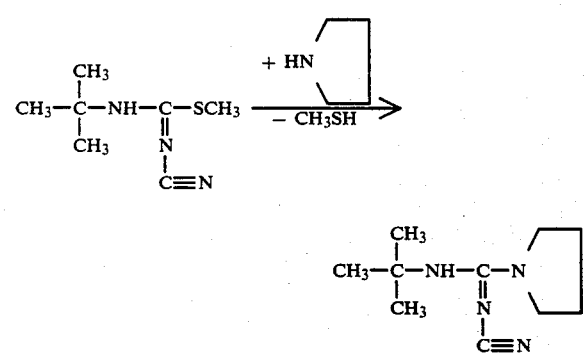

Particularly preferred thioureas to be used as starting compounds of formula (II) for process variant (a) according to the invention are those in which $R^1$, $R^2$ and $R^3$ represent those radicals which have already been mentioned for these substituents in connection with the description of the preferred and particularly preferred compounds of the present invention.

The thioureas of the formula (II) are generally known compounds of organic chemistry.

The heavy metal salts of cyanamide which are also required as starting substances for process variant (a) according to the invention are likewise known. Lead salts, mercury salts and cadmium salts are preferably employed as the heavy metal salts.

Particularly preferred amidines to be used as starting compounds of formula (III) for process variant (b) according to the invention are those in which X represents a chlorine or bromine atom or a methoxy or methylmercapto radical and $R^2$ and $R^3$ represent those radicals which have already been mentioned for these substituents in connection with the description of the preferred and particularly preferred compounds of the present invention.

Amidines of the formulae (III) and (V) are known; they can be obtained in a generally known manner, for example by reacting 1 mole of a cyanamidodithiocarbonic acid dialkyl ester with 1 mole of an appropriate amine in the presence of a polar solvent, such as an alcohol, at a temperature between 0° and 150° C., 1 mole of alkylmercaptan being split off.

Preferred possible diluents for the reaction, according to the invention, in process variant (a) are inert organic solvents. These include, preferably, monohydric alcohols, such as methanol and ethanol, but also polyhydric alcohols, such as glycol, and esterified derivatives thereof; ethers, such as tetrahydrofuran and dioxane; nitriles, such as acetonitrile; and amides, such as dimethylformamide and dimethylacetamide.

If appropriate, process variant (a) according to the invention is carried out in the presence of a phase transfer catalyst, such as ammonium or phosphonium compounds, for example, triethyl-benzyl-ammonium chloride.

The reaction temperatures can be varied within a substantial range in carrying out process variant (a) according to the invention. In general, the reaction is carried out between 50° and 200° C., preferably between 70° and 160° C.

In carrying out process variant (a) according to the invention, 2 moles of heavy metal salt of cyanamide and, if appropriate, 0.01 to 0.1 mole of the phase transfer catalyst are preferably employed per mole of thiourea of the formula (II). The compounds of the formula (I) are isolated in the customary and known manner.

In a particular embodiment of process variant (a) according to the invention, heavy metal sulphide which is formed is intermediately filtered off, together with cyanamide which has not yet reacted, and fresh cyanamide and, if appropriate, also phase transfer catalyst are added again.

Preferred possible diluents for the reaction, according to the invention, in process variants (b) and (c) are polar organic solvents. These include, preferably, alcohols, such as methanol and ethanol; ether, such as diethyl ether, dioxane and tetrahydrofuran; nitriles, such as acetonitrile; and amides, such as dimethylformamide.

The reaction temperatures can be varied within a substantial range in carrying out variants (b) and (c) according to the invention. In general, the reactions are carried out between 0° and 150° C., preferably between 20° and 150° C.

Molar amounts are preferably used in carrying out processes (b) and (c) according to the invention. The compounds of the formula (I) are isolated in the generally customary and known manner.

As well as by the process variants (a), (b) and (c) mentioned, the substances of the formula (I) according to the invention can also be obtained by other, generally known process variants, such as, for example, by reacting amidines of the formula.

in which
  $R^1$, $R^2$, $R^3$ and X have the abovementioned meaning, with cyanamide in the generally customary and known manner, or by reacting guanidines of the formula

in which $R^1$, $R^2$ and $R^3$ have the abovementioned meaning, with cyanogen bromide or chloride in the generally customary and known manner.

The following acids can preferably be used for the preparation of physiologically acceptable acid addition salts of the compounds of the formula (I): hydrogen halide acids (such as hydrobromic acid and, in particular, hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid), and sulphonic acids (such as p-toluenesulphonic acid and 1,5-naphthalenedisulphonic acid). The acid addition salts of the compounds of the formula (I) can be obtained in a simple manner by customary salt formation methods, for example by dissolving a compound of the formula (I) in a suitable inert solvent and adding the acid, for example hydrogen chloride, and they can be isolated in a known manner, for example by filtration, and if appropriate purified by washing with an inert organic solvent.

Thr active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Oomycetes, for example against the causative organism of blight and brown rot of tomato and potato (*Phytophthora infestans*). It should be particularly emphasised that the active compounds according to the invention have not only a protective action but also a systemic action. It is thus possible to protect plants from fungal attack if the active compound is fed to the above-ground parts of the plant via the soil and the root or via the seed.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquified gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulstions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.0001 to 0.02%, are generally required at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLE

EXAMPLE 1

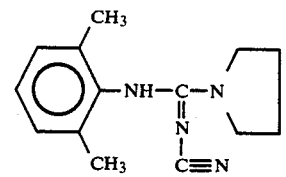

(Process variant (a))

247.2 g (1 mole) of lead cyanamide were added to a solution of 234.4 g (1 mole) of N'-(2,6-dimethylphenyl)-N,N-tetramethylene-thiourea in 1,000 ml of dimethylformamide. The reaction mixture was stirred at 135° C. for 48 hours. During this period, in each case a further 123.6 g (0.5 mole) of lead cyanamide were added after 7 and 17 hours. The reaction mixture was filtered hot, the filtrate was concentrated and the residue was recrystallized from ethanol. 148.6 g (61.3% of theory) of N''-cyano-N'-(2,6-dimethylphenyl)-N,N-tetra-methylene-guanidine of melting point 192° to 194° C. were obtained.

The following compounds of the general formula

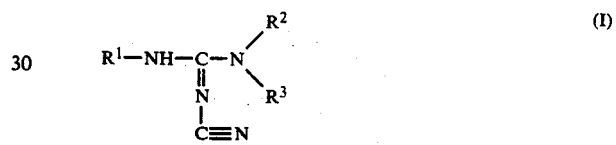

were obtained in an analogous manner and according to process variant (a), (b) and (c) as described in the text:

| Compound No. | $R^1$ | $R^2$ | $R^3$ | Melting point (°C.) |
|---|---|---|---|---|
| 2 | 2,6-$(CH_3)_2$—$C_6H_3$ | $CH_3$ | $CH_3$ | 246–47 (decomposition) |
| 3 | 4-Cl, 2-$CH_3$—$C_6H_3$ | $CH_3$ | $CH_3$ | 205–07 |
| 4 | 2-Cl, 6-$CH_3$—$C_6H_3$ | $CH_3$ | $CH_3$ | 243–44 |
| 5 | 2,6-(i-$C_3H_7$)$_2C_6H_3$ | $CH_3$ | $CH_3$ | 218–19 |
| 6 | 2,4,6-$(CH_3)_3$—$C_6H_2$ | $CH_3$ | $CH_3$ | 230–32 |
| 7 | 2,6-$(CH_3)_2$—$C_6H_3$ | —$(CH_2)_5$— | | 196–98 |
| 8 | 2,6-$(CH_3)_2$—$C_6H_3$ | $C_2H_5$ | $C_2H_5$ | 169–75 |
| 9 | 2-Cl, 6-$CH_3$—$C_6H_3$ | —$(CH_2)_5$— | | 165–68 |
| 10 | 2,4,6-$(CH_3)_3$—$C_6H_2$ | —$(CH_2)_4$— | | 161 |
| 11 | 2,6-$(CH_3)_2$—$C_6H_3$ | —$(CH_2)_2$—O—$(CH_2)_2$— | | 192–95 |
| 12 | $C_6H_5$ | —$(CH_2)_4$— | | 166–168 |
| 13 | $C_6H_5$ | $CH_3$ | $CH_3$ | 162–64 |
| 14 | 2,6-$Cl_2$—$C_6H_3$ | —$(CH_2)_2$—O—$(CH_2)_2$— | | 212 |
| 15 | 2,6-$(C_2H_5)_2$—$C_6H_3$ | —$(CH_2)_4$— | | 176–78 |
| 16 | 2-$C_2H_5$, 6-$CH_3$—$C_6H_3$ | —$(CH_2)_4$— | | 165–68 (decomposition) (× HCl) |
| 17 | 2,6-$(CH_3)_2$—$C_6H_3$ | —$(CH_2)_6$— | | 176–80 |
| 18 | 2-Cl, 6-$CH_3$—$C_6H_3$ | —$(CH_2)_4$— | | 190–92 |
| 19 | 2,6-$(CH_3)_2$—$C_6H_3$ | $C_3H_7$ | $C_3H_7$ | 89–92 |
| 20 | 2-$CH_3$, 6-$OCH_3$—$C_6H_3$ | —$(CH_2)_4$— | | 153–54 |
| 21 | 2-$CH_3$—$C_6H_4$ | —$(CH_2)_4$— | | 155–57 |
| 22 | 2-$CF_3$—$C_6H_4$ | —$(CH_2)_4$— | | 143–44 |
| 23 | 2,5-$(CH_3)_2$—$C_6H_3$ | —$(CH_2)_4$ | | 177–78 |
| 24 | 2,3-$(CH_3)_2$—$C_6H_3$ | —$(CH_2)_4$— | | 186–90 |
| 25 | 2,4-$(CH_3)_2$—$C_6H_3$ | —$(CH_2)_4$— | | 157–59 |
| 26 | 3,4-$(CH_3)_2$—$C_6H_3$ | —$(CH_2)_4$— | | 172–75 |
| 27 | 2-$OCH_3$, 4-$CH_3$—$C_6H_3$ | —$(CH_2)_4$— | | 178–81 |
| 28 | 3-Cl—$C_6H_4$ | —$(CH_2)_4$— | | 128–31 |
| 29 | 4-Br—$C_6H_4$ | —$(CH_2)_4$— | | 227–30 |

The fungicidal activity of the compounds of this invention is illustrated by the following examples, wherein the compounds according to the present invention are each identified by the number (given in brackets) from Example 1 and the table hereinabove.

The known comparison compounds are identified as follows:

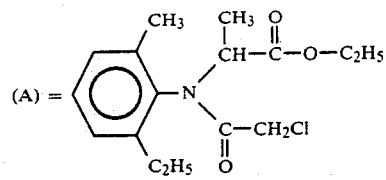

N-Chloroacetyl-N-(2-ethyl-6-methyl-phenyl)-alanine ethyl ester.

EXAMPLE 2

Phytophthora test (tomatoes)/protective
Solvent: 4.7 parts by weight of acetone
Emulsifier: 0.3 part by weight of alkylaryl polyglycol ether
Water: 95.0 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were sprayed with the spray liquid until dripping wet. The plants remained in a greenhouse for 24 hours at 20° C. and at a relative atmospheric humidity of 70%. The tomato plants were then inoculated with an aqueous spore suspension of *Phytophthora infestans*. The plants were brought into a humidity chamber with an atmospheric humidity of 100% and a temperature of 18° to 20° C.

After 5 days the infection of the tomato plants was determined. The assessment data were converted to percent infection. 0% denoted no infection and 100% denoted that the plants were totally infected.

In this test, for example, the following compounds exhibited a very good action which was significantly superior to that of the compound (A) known from the prior art: compounds (1), (2) and (8).

EXAMPLE 3

Phytophthora test (tomatoes)/systemic
Solvent: 4.7 parts by weight of acetone
Dispersing agent: 0.3 part by weight of alkylaryl polyglycol ether
Water: 95.0 parts by weight The amount of the active compound required for the desired concentration of the active compound in the watering liquid was mixed with the stated amount of solvent and the concentrate was diluted with the stated amount of water which contained the stated additions.

Tomato plants grown in standard soil and having 2 to 4 foliage leaves were watered with 10 ml of the watering liquid, having the stated concentration of active compound, per 100 ml of soil.

The plants treated in this way were inoculated, after the treatment, with an aqueous spore suspension of *Phytophthora infestans*. The plants were brought into a humidity chamber at an atmosphere humidity of 100% and a temperature of 18° to 20° C. After 5 days, the infection of the tomato plants was determined. The assessment data were converted to percent infection. 0% denoted no infection and 100% denoted that the plants are totally infected.

In this test, for example, the following compounds exhibited a very good action which was significantly superior to that of the compound (A) known from the prior art: compounds (1), (2), (3), (4), (8) and (9).

It will be understood that the specification and examples are illustrative but not limitative of the present invention and that other embodiments within the spirit and scope of the invention will suggest themselves to those skilled in the art.

We claim:

1. A method of combating fungi comprising applying to the fungi, or to a habitat thereof, a fungicidally effective amount of a trisubstituted cyanoguanidine of the formula

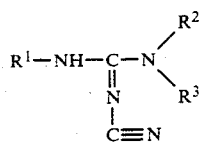

in which $R^1$ represents a phenyl radical which is optionally monosubstituted or polysubstituted by identical or different substituents which are selected from fluorine, chlorine, bromine, iodine, methyl, ethyl, n-propyl, isopropyl, vinyl, methoxy, methylthio, ethoxy, n-propoxy, isopropoxy, trifluoromethyl, nitro, cyano, amino, hydroxy, dimethylamino, acetyl, methylsulphonyl, carbamoyl, aminosulphonyl, phenyl, chlorophenyl, phenoxy, chlorophenoxy, benzyloxy, chlorobenzyloxy, methylaminomethyl, dimethylaminomethyl, methylaminoethyl, dimethylaminoethyl, acetylamino and acetyl-methyl-amino; $R^2$ represents a methyl, ethyl, n-propyl, isopropyl, hydroxyethyl, cyanoethyl or allyl radical; $R^3$ represents a methyl, ethyl, n-propyl, isopropyl, hydroxyethyl, cyanoethyl, allyl or cyclopentyl radical, a cyclohexyl radical which is optionally substituted by methyl or ethyl, or an optionally substituted phenyl or benzyl radical, the substituents being selected from fluorine, chlorine, bromine, methyl, ethyl, methoxy, nitro and cyano; or $R^2$ and $R^3$, together with the nitrogen atom to which they are bonded, represent a pyrrolidine, piperidine or morpholine ring which is optionally substituted by methyl or a fused-on benzene ring; or a physiologically acceptable acid addition salt thereof.

2. A method according to claim 1, in which $R^1$ represents a phenyl radical which is optionally monosubstituted or polysubstituted by identical or different substituents which are selected from fluorine, chlorine, bromine, iodine, methyl, ethyl, n-propyl, isopropyl, vinyl, methoxy, methylthio, ethoxy, n-propoxy, isopropoxy, nitro, cyano, amino, hydroxy, dimethylamino, acetyl, methylsulphonyl, carbamoyl, aminosulphonyl, phenyl, chlorophenyl, phenoxy, chlorophenoxy, benzyloxy, chlorobenzyloxy, methylaminomethyl, dimethylaminomethyl, methylaminoethyl, dimethylaminoethyl, acetylamino and acetyl-methyl-amino; or a physiologically acceptable acid addition salt thereof with a hydrogen halide acid, phosphoric acid, nitric acid, sulphuric acid, a monofunctional or bifunctional carboxylic acid or hydroxycarboxylic acid or a sulphonic acid.

3. The method according to claim 2, wherein said compound is

N''-cyano-N'-(2,6-dimethylphenyl)-N,N-tetra-methylene-guanidine,

N''-cyano-N'-(2,6-dimethylphenyl)-N,N-dimethyl-guanidine,

N''-cyano-N'-(2-chloro-6-methyl-phenyl)-N,N-dimethyl-guanidine, or

N''-cyano-N'-(2,6-dichlorophenyl)-N,N-diethyl-guanidine.

4. A compound selected from the group consisting of N''-cyano-N'-(2,6-dimethylphenyl)-N,N-tetramethyleneguanidine, N''-cyano'N'-(2,6-dimethylphenyl)-N,N-dimethylguanidine, N''-cyano-N'-(2-chloro-6-methylphenyl)-N,N-dimethyl-guanidine and N''-cyano-N'-(2,6-dichlorophenyl)-N,N-diethyl-guanidine, or a physiologically acceptable acid addition salt thereof.

5. A compound according to claim 1, wherein such compound is N''-cyano-N'-(2,6-dimethylphenyl)-N,N-tetramethylene-guanidine of the formula

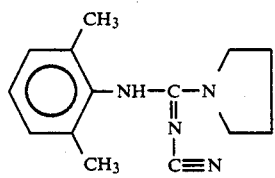

or a physiologically acceptable acid addition salt thereof.

6. A compound according to claim 1, wherein such compound is N''-cyano-N'-(2,6-dimethylphenyl)-N,N-dimethylguanidine of the formula

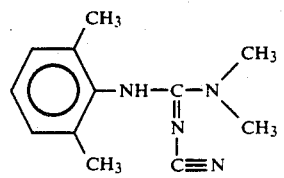

or a physiologically acceptable acid addition salt thereof.

7. A compound according to claim 1, wherein such compound is N''-cyano-N'(2-chloro-6-methyl-phenyl)-N,N-dimethyl-guanidine of the formula

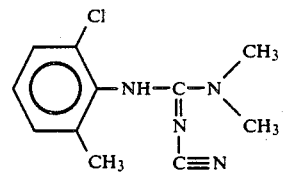

or a physiologically acceptable acid addition salt thereof.

8. A compound according to claim 1, wherein such compound is N''-cyano-N'-(2,6-dichlorophenyl)-N,N-diethylguanidine of the formula

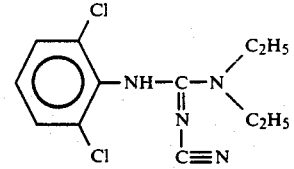

or a physiologically acceptable acid addition salt thereof.

* * * * *